United States Patent
Sturgis et al.

(10) Patent No.: US 11,833,232 B2
(45) Date of Patent: Dec. 5, 2023

(54) DEODORANT COMPOSITIONS WITH NATURAL WAX

(71) Applicant: The Procter & Gamble Company, Cincinnati, OH (US)

(72) Inventors: David Arthur Sturgis, Montgomery, OH (US); Lindsey Michelle Britt, Deer Park, OH (US); Mahmoud Daffalla Eljack, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 159 days.

(21) Appl. No.: 17/409,955

(22) Filed: Aug. 24, 2021

(65) Prior Publication Data

US 2022/0054366 A1 Feb. 24, 2022

Related U.S. Application Data

(60) Provisional application No. 63/069,209, filed on Aug. 24, 2020.

(51) Int. Cl.

| | |
|---|---|
| *A61K 8/02* | (2006.01) |
| *A61K 8/19* | (2006.01) |
| *A61K 8/34* | (2006.01) |
| *A61K 8/37* | (2006.01) |
| *A61K 8/92* | (2006.01) |
| *A61Q 15/00* | (2006.01) |
| *A61Q 17/00* | (2006.01) |

(52) U.S. Cl.
CPC .............. *A61K 8/0229* (2013.01); *A61K 8/19* (2013.01); *A61K 8/342* (2013.01); *A61K 8/37* (2013.01); *A61K 8/375* (2013.01); *A61K 8/92* (2013.01); *A61Q 15/00* (2013.01); *A61Q 17/005* (2013.01); *A61K 2800/30* (2013.01); *A61K 2800/31* (2013.01)

(58) Field of Classification Search
None
See application file for complete search history.

(56) References Cited

U.S. PATENT DOCUMENTS

| | | | | |
|---|---|---|---|---|
| 5,723,110 | A | * | 3/1998 | Yamamoto ............... A61K 8/26 424/617 |
| 5,744,130 | A | * | 4/1998 | Guskey .................... A61K 8/28 424/68 |
| 6,488,919 | B1 | | 12/2002 | Murphy et al. |
| 6,652,843 | B2 | | 11/2003 | Fairclough et al. |
| 8,673,327 | B2 | | 3/2014 | Lemoine et al. |
| 10,470,999 | B2 | | 11/2019 | Lesniak et al. |
| 10,555,884 | B2 | * | 2/2020 | Sturgis ................... A61K 8/347 |
| 2010/0104612 | A1 | | 4/2010 | Cropper |
| 2012/0039833 | A1 | | 2/2012 | Brennan et al. |
| 2012/0045493 | A1 | | 2/2012 | Popoff et al. |
| 2016/0081895 | A1 | | 3/2016 | Elliott et al. |
| 2018/0168947 | A1 | | 6/2018 | Banowski et al. |
| 2018/0168985 | A1 | | 6/2018 | Banowski et al. |
| 2019/0105239 | A1 | | 4/2019 | Mikkelsen et al. |
| 2019/0105255 | A1 | | 4/2019 | Mikkelsen et al. |
| 2019/0336434 | A1 | | 11/2019 | Li |
| 2019/0350824 | A1 | | 11/2019 | Moujahed et al. |
| 2020/0016053 | A1 | | 1/2020 | Hilliard, Jr. et al. |
| 2022/0054375 | A1 | | 2/2022 | Sturgis et al. |

FOREIGN PATENT DOCUMENTS

| | | |
|---|---|---|
| DE | 102008052747 A1 | 4/2010 |
| DE | 102018220966 A1 | 6/2020 |
| EP | 2189149 A1 | 5/2010 |
| WO | 20180122209 A1 | 7/2018 |
| WO | 2020000069 A1 | 1/2020 |

OTHER PUBLICATIONS

PCT Search Report and Written Opinion for PCT/US2021/047278 dated Jan. 18, 2022, 17 pages.
Non-Final office action; U.S. Appl. No. 17/409,955, dated May 25, 2023.

* cited by examiner

*Primary Examiner* — Melissa S Mercier
(74) *Attorney, Agent, or Firm* — Alexandra S. Anoff

(57) ABSTRACT

A deodorant stick comprising: a natural or naturally-derived oil; an antimicrobial; a naturally-derived wax blend comprising from about 5% to about 20% an ester wax having a melting point of at least about 55° C.; and from 0.01% to 2% a fatty alcohol or fatty alcohol-containing wax; wherein the deodorant stick is anhydrous and substantially free of aluminum; and wherein the stick has an oil binding capacity percent of at least 80%.

20 Claims, No Drawings

DEODORANT COMPOSITIONS WITH NATURAL WAX

FIELD OF THE INVENTION

The present disclosure relates to deodorant compositions and methods relating thereto.

BACKGROUND OF THE INVENTION

Many consumers are seeking more natural, aluminum-free deodorant offerings, often mostly free of silicones, that are also made with natural or naturally-derived waxes. Consumers also want a good glide, non-sticky, and non-greasy application. This is a challenge, because a mostly silicone-free formula will often use natural oils or natural oil-based triglycerides. Many natural waxes are not ideal or compatible for formulating with these natural oils to create a stick that is consumer acceptable in feel, stable at high and low temperatures, and uniform in hardness throughout the stick.

Thus there remains a challenge to formulate with natural or naturally-derived waxes an aluminum-free, mostly silicone-free deodorant stick that is more uniform in hardness, and therefore more uniform in feel during the usage of the stick.

SUMMARY OF THE INVENTION

A deodorant stick comprising: a natural or naturally-derived oil; an antimicrobial; a naturally-derived wax blend comprising from about 5% to about 20% an ester wax having a melting point of at least about 55° C.; and from 0.01% to 2% a fatty alcohol or fatty alcohol-containing wax; wherein the deodorant stick is anhydrous and substantially free of aluminum; and wherein the stick has an oil binding capacity percent of at least 80%.

DETAILED DESCRIPTION OF THE INVENTION

While the specification concludes with claims that particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more". Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "anhydrous" as used herein means substantially free of added or free water. From a formulation standpoint, this means that the anhydrous deodorant stick compositions of the present invention contain less than about 1%, and more specifically zero percent, by weight of free or added water, other than the water of hydration typically associated with the particulate deodorant active prior to formulation.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

As consumers seek more natural ingredients in their deodorants, one approach to formulation is to use emollients derived from natural oils. Emollients derived from natural oils are derived from plant sources, such as palm oil or coconut oil. One example of an emollient derived from natural oils may be a liquid triglyceride, defined as liquid at 25° C. Thus, products that hope to emphasize natural ingredients may have a significant amount of a liquid triglyceride, for example.

In order to provide structure to the deodorant stick composition, the formulation may also include a number of waxes and other structurants. While many synthetic or petroleum-based waxes can suitably be used for this purpose, it is a significant challenge to find a wax or wax combination that is natural or naturally-derived.

It is known that to formulate a solid deodorant stick, the structurants generally have a melting point above 50° C. to provide a stable structure to the stick. A stick typically would have wax sufficient enough to produce a hardness of less than 140 mm*10, as measured by penetration under ASTM D-5 needle, alternatively less than 100 mm*10, alternatively less than 70 mm*10, and in some embodiments, less than 60 mm*10, as measured by penetration under ASTM D-5 needle.

Consumers also want the hardness to be uniform throughout the stick so that the consumer experience does not change over the usage of the product. Surprisingly, ester-based wax sticks are difficult to produce a uniform, hard, crystal structure throughout the stick.

Efficacy Enhancement

The primary function of many deodorants is to release a high-pH powder that will inhibit the growth of odor-causing bacteria. The most consumer-preferred form of these deodorants is in a solid stick solidified by structurants. Structurants, like waxes, are used in this form to help give the stick its structure and stability. The downside of structurants is that they tend to interfere with the release of the high-pH powdered active from the composition and thus negatively impact the efficacy of the product. This issue is compounded as some consumers desire deodorant sticks made of natural or naturally-derived oils that are non-volatile, which can further impede pH release.

While reductions in structurant level could be used to help increase active efficacy, this comes with its own challenges. Reducing the structurant level, for example, can negatively impact the stability of the product. As such, the desired solution is to find something that could be added to these types of solid products that would enhance water transport through the product film without negatively impacting stability of the product. Initial work focused on finding structurants and natural or naturally-derived oils whose water solubility and water transport properties lessened the impact of the release of high pH powders.

Consumers seeking aluminum free, naturally derived deodorants are also seeking products that are free from controversial ingredients, due to publicity around the ingredients' safety, farming, or labor practices. Therefore, in some embodiments, it may be ideal to have the deodorant free from solvents or emollients such as, for example, isopropyl palmitate, ppg-14 butyl ether, coconut oil, almond oil, palm kernel oil, propanediol, propylene glycol, and/or silicones.

In some embodiments, it may be ideal to have the deodorant free from certain waxes, such as, for example, beeswax, stearyl alcohol, behenyl alcohol, candelilla wax, and/or carnauba wax. In some embodiments, it may be ideal to have the deodorant free from powders such as calcium hydroxide, sodium bicarbonate, magnesium hydroxide, arrowroot powder, and/or corn starch. In some embodiments, it may be ideal to have the deodorant free from all fatty acid ester oils like isopropyl myristate. In some embodiments, it may be ideal to have the deodorant free from palm-derived materials. In some embodiments, it may be ideal to have the deodorant free from triheptanoin.

A. Structurants

The deodorant compositions of the present invention may comprise a suitable concentration of structurants to help provide the compositions with the desired viscosity, rheology, texture and/or product hardness, or to otherwise help suspend any dispersed solids or liquids within the composition.

The desire for natural or naturally derived emollients combined with natural or naturally derived structurants to avoid petroleum-derived ingredients is growing. However, the more natural or naturally derived the emollient and wax become, often the more complicated the interactions between the two. During crystallization, various molecular rearrangements may occur. Such rearrangements result in differing crystalline material properties, such as hardness, viscoelasticity, and oil encapsulation efficiency. Inter-molecular forces, such as van der Waals forces, hydrogen bonds, and London dispersion forces, can play a role in co-crystallization of waxes.

A simple base case of a paraffin wax and mineral oil has minimal interactions between the two to cause rearrangement, because of their limited intermolecular forces with straight carbon chains without any complex bends caused by double bonds or additional functional groups like esters. Potential interactions between a natural or natural derived oil and a natural or natural derived wax can be much more complicated.

Specifically, with ester-based waxes, this interaction and polymorphism can create solid sticks that appear to be consumer acceptable on the top of the stick (when poured into a bottom fill package), but consumer unacceptable and significantly softer with lower oil absorption in the middle that takes longer to cool and crystalize towards the middle and bottom of the stick. The ester group makes the wax crystal look like a caret '^'. When cooling fast, like at the interface between the hot poured product and the ambient canister, the crystals cool too fast to have time to rearrange in relation to each other. Therefore, they will be in a random orientation relative to their neighbor crystals. This will lead to times where the carbon chains can connect or bridge together to form a harder structure capable of binding the emollient oils more efficiently.

However, the middle of the canister towards the bottom will cool the slowest since it is insulated from the ambient air. Here, the same wax crystals have time for inter-molecular forces, such as van der Waals forces, hydrogen bonds, and London dispersion forces to cause rearrangement of the wax crystals. These carets '^' will stack on top of each other like bowls stacked in a kitchen cabinet. This rearrangement minimizes the potential for carbon chains to connect or bridge together, and results in significantly softer stick regions with significantly worse oil absorption. This can be seen by pressing a finger into the wax and visually observing a more mushy stick where the oil will often weep out from the minimal force exerted.

The addition of a secondary fatty alcohol-containing wax creates an additional co-crystallization where the carbon chain of the fatty alcohol will not rearrange in the same way in the presence of the ester wax, and can connect or bridge across the ester based waxes, even after they have rearranged with each other. In some embodiments it is preferred to use rice bran wax. In this way, customer confusion over "alcohol" on the ingredient statement is avoided. This also results in a more homogenous stick that can have more consistent oil binding capacity throughout, which will give a more consistent and consumer preferred experience throughout the life of the stick.

This is why some combinations of natural ingredients combine to form consumer-unacceptable sticks, either solid sticks that are insufficiently hard, or sticks that are not homogeneous, as the cooling rate from the outside of the stick to the inside affects the time and extent of rearrangement. Waxes with a melting point above 50° C. or higher tend to have higher molecular weights and are associated with harder sticks even after some crystal rearrangement occurs. This can show up as the top of the stick (closer to the air or cold plastic) having a hardness different than the bottom of the stick (most insulated and last to cool).

The primary structurant in the present invention may be an ester wax with a melting point of at least about 50° C., in some embodiments from about 55° C. to about 85° C., and in other embodiments from about 55° C. to about 80° C., and in other embodiments from about 60° C. to 80° C. Ester waxes with melting points between 50° C. and 85° C. include stearyl stearate, palmityl stearate, stearyl behenate, cetearyl behenate, behenyl behenate, stearyl stearate, and combinations thereof. Waxes outside of this melting range often result in stick compositions that are too soft. Wax levels below about 5% result in products that are too soft. And levels above 20% are often too draggy to have consumer acceptable application.

A primary structurant is defined as the structurant that is present in the composition in the greatest amount (liquid triglycerides are not considered a structurant in this context). Some embodiments may have just a single structurant, so may have only a primary structurant. Other embodiments may have a primary structurant and then secondary structurants, those structurants that are used in a lesser amount than the primary structurant.

The primary structurant may comprise from about 5% to about 20%, in some cases from about 7% to about 17%, by weight of the deodorant stick composition. The secondary structurants may cumulatively comprise about 0.01% to about 2%, by weight of the deodorant stick.

In some embodiments, some secondary structurants may be fatty alcohol-containing waxes. Examples of fatty alcohol-containing waxes include rice bran wax, stearyl alcohol, behenyl alcohol, cetly alcohol, oleyl alcohol, arachidyl alcohol, ceryl alcohol, and combinations thereof.

The term "structurant" as used herein means any material known or otherwise effective in providing suspending, gelling, viscosifying, solidifying, and/or thickening properties to the composition or which otherwise provide structure to the final product form.

As shown in Table 1, Inventive Examples 1 and 2 and Comparative Example 1 each have 11% of a wax ester (behenyl behenate). But only the inventive examples also have a fatty alcohol (or a fatty alcohol-containing wax, such as rice bran wax). Without the fatty alcohol or fatty alcohol-containing wax, the consistency of the Comparative Example 1 stick becomes too soft in its center (the center of the bottom of the stick), while the center of each of Inventive Examples 1 and 2 is firm. This is most evident in the difference in Oil Binding Capacity. The hardness of Inventive Examples 1 and 2 at the top and bottom of the stick are also acceptable, as the hardness readings are below 60 mm*10. The top and bottom stick hardness for all the Comparative Examples, including Comparative Example 1, are above 60 mm*10, meaning softer sticks. Table 1 also shows that in Comparative Examples 2, 3, and 5, higher amounts of ester wax alone, in this case 17%, 14%, and 20% respectively, by weight of the composition, can make the deodorant stick too soft at the top, bottom, and center of the bottom of the stick. Inventive Example 4 shows that the ester wax amount can be as low as 5% by weight of the composition and, as long as combined with a fatty alcohol, results in an acceptably firm deodorant stick. It can be that if the ester wax amount is below 5% by weight of the composition, even if combined with a fatty alcohol, the stick is too soft and unacceptable to consumers. Compositions above 20% ester wax with some fatty alcohol are generally too hard to be cosmetically acceptable. All hardness data herein is generated via the Hardness Test Method described below.

Also shown in Table 1 is the oil binding capacity percent. A non-homogenous stick will have a lower oil binding capacity percent, that is, where the oil in the stick is less cohesive with the rest of the stick. A non-homogeneous stick that has a mushy center of the bottom can be pressed with a finger, and the oil may be seen pressed out of the wax due to the force. Often a larger variation in hardness from top to bottom may signal heterogeneity. Looking at Table 1, the Inventive Examples have an oil binding capacity percent of greater than 80%, while the Comparative Examples are 72.1 or lower. By adding a small amount of a fatty alcohol or a fatty alcohol-containing wax to the system, such as 0.01-2% by weight of the composition, homogeneity is significantly improved, as evidenced by the oil binding increase, the firmness vs mushy center, and the lower hardness and less difference between top and bottom hardness, as shown in Comparative Example 1 vs Inventive Examples 1 or 2. The oil binding capacity percent data is generated via the Oil Binding Capacity Test Method described below. These differences in oil binding capacity will have both a significant impact in consumer acceptance, where the lower comparative oil binding capacities will result in a mushier, and greasy stick in application and throughout the life of the stick, as well as the hot and cold stability of the stick through transportation. Lower oil binding capacities risk significantly more oil weeping out of the product when at the high and low extreme temperatures that could be seen during a polar vortex or summer heat dome weather events. Additionally, lower oil binding capacity sticks also risk more negative consumer comments regarding oil staining of clothes, even more so with the natural or naturally derived oils that are desired by some consumers.

| Ingredient | Inventive #1 | Inventive #2 | Inventive #3 | Inventive #4 | Inventive #5 | Inventive #6 | Inventive #7 |
|---|---|---|---|---|---|---|---|
| Coconut Oil Fractionated (Caprylic/capric triglyceride) | 51.850 | 51.900 | 54.000 | 63.000 | 54.950 | | |
| Triheptanoin | | | | | | 66.800 | 62.500 |
| Behenyl Behenate | 11.000 | 11.000 | 7.000 | 5.000 | 20.000 | | |
| Steaeryl Behenate | | | | | | 8.000 | 12.000 |
| Magnesium Oxide | 8.000 | 8.000 | 8.000 | 8.000 | 8.000 | 8.000 | 8.000 |
| Tapioca Starch | 27.000 | 27.000 | 27.000 | 20.000 | 15.000 | 15.000 | 15.000 |
| Rice Bran Wax | 0.150 | 0.100 | 2.000 | 2.000 | 0.050 | 0.200 | 0.500 |
| Essential Oils | 2.000 | 2.000 | 2.000 | 2.000 | 2.000 | 2.000 | 2.000 |
| Hardness of Top of Stick (mm * 10) | 33.9 | 28.4 | 58.6 | 115 | 37 | 27 | 58 |
| Hardness of Bottom of Stick (mm * 10) | 32.8 | 41.4 | 53.8 | 115 | 37 | 25.2 | 57 |

-continued

| | | | | | | | |
|---|---|---|---|---|---|---|---|
| Center Firm or Mushy to touch | Firm | Firm | Firm | Firm | Firm | Firm | Firm |
| Average % Oil Binding Capacity of (Top/Middle/Bottom | 85.1 | 80.9 | 91.9 | 86.3 | 80.4 | 82.4 | 89.4 |

| Ingredient | Comparative #1 | Comparative #2 | Comparative #3 | Comparative #4 | Comparative #5 | Comparative #6 | Comparative #7 |
|---|---|---|---|---|---|---|---|
| Coconut Oil Fractionated (Caprylic/capric triglyceride) | 52.000 | 53.000 | 56.000 | 65.000 | 55.000 | | |
| Triheptanoin | | | | | | 67.000 | 63.000 |
| Behenyl Behenate | 11.000 | 17.000 | 14.000 | 5.000 | 20.000 | | |
| Steaeryl Behenate | | | | | | 8.000 | 12.000 |
| Magnesium Oxide | 8.000 | 8.000 | 8.000 | 8.000 | 8.000 | 8.000 | 8.000 |
| Tapioca Starch | 27.000 | 20.000 | 20.000 | 20.000 | 15.000 | 15.000 | 15.000 |
| Rice Bran Wax | | | | | | | |
| Essential Oils | 2.000 | 2.000 | 2.000 | 2.000 | 2.000 | 2.000 | 2.000 |
| Hardness of Top of Stick (mm * 10) | 73 | 65 | 86 | >250 | 55 | >250 | 92 |
| Hardness of Bottom of Stick (mm * 10) | 108 | 73 | 92 | >250 | 61 | >250 | 97 |
| Center Firm or Mushy to touch | Mushy | Mushy | Mushy | All Mushy | Press and liquid comes out | Mushy | Mushy |
| Average % Oil Binding Capacity of (Top/Middle/Bottom) | 64.7 | 72.1 | 61.3 | 50.8 | 65.4 | 47.1 | 54.4 |

B. Emollients

The composition may include a natural or naturally-derived oil. The natural or naturally-derived oil may be a plant oil. The term "plant oil" means that the oil is obtained from a plant, or the plant oil can be made by blending of oil components to obtain an oil that is substantially similar in composition to a plant oil. By substantially similar, it is meant that the manufactured oil contains at least 50 weight % (or at least 60, 70, 80, 90, 95, 98, or 99 weight %) of the components that are found in the plant oil that it is designed to mimic. In certain embodiments, the plant oil has a melting point below 40° C., below 35° C., or below 30° C. Examples of the plant oil include, but are not limited to, palm kernel, coconut, avocado, canola, corn, cottonseed, olive, palm, hi-oleic sunflower, mid-oleic sunflower, sunflower, palm stearin, palm kernel olein, safflower, babassu oils, and combinations thereof. In one embodiment, palm kernel oil may be the selected oil. In another embodiment, coconut oil may be the selected oil. In another embodiment, the plant oil may be a combination of palm kernel oil and coconut oil.

As discussed, an effective and consumer-preferred emollient may be a liquid triglyceride. Derived directly from plant sources, they are often short chains. Longer chain triglycerides may be used as structurants in deodorant or antiperspirant sticks, but the triglycerides of the present invention are liquid at room temperature (25° C.) and tend to be shorter chains. An example may be caprylic/capric triglyceride (coconut oil fractionated) and/or triheptanoin. In some embodiments, the liquid triglyceride may have a mixture of chain lengths from 8 to 10, or C8-C10 triglycerides.

The present inventive deodorant sticks may comprise at least about 20% of one or more liquid triglyceride, in some embodiments, at least about 25%, at least about 30%, at least 35%, at least about 40%, at least about 45%, or at least about 50% liquid triglyceride, by weight of the composition. In some embodiments, the deodorant stick comprises from about 25% to about 60%, by weight of the composition, of one or more liquid triglyceride, from about 25% to about 50%, from about 30% to about 50%, from about 35% to about 60%, from about 35% to about 50%, from about 40% to about 60%, or from about 40% to about 50%, by weight of the composition, of one or more liquid triglyceride. In general, the greater amount of liquid in the formulation, the softer the deodorant stick may be. The more solids in the formulation leads to greater hardness. Because achieving a sufficient softness in a deodorant stick with natural ingredients can be a challenge, it can be beneficial to formulate with higher amounts of liquids such as liquid triglyceride. The level of liquid triglyceride as referred to herein may be the sum total of one or more types of liquid triglyceride in a particular deodorant stick.

In some embodiments, additional emollients may be used, such as plant oils (generally used at less than about 10% by weight of the composition) including olive oil, coconut oil, sunflower seed oil, jojoba seed oil, avocado oil, canola oil, and corn oil. Additional emollients including mineral oil; shea butter, PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone, and any mixtures thereof.

C. Antimicrobials

The present invention may include one or more antimicrobial compositions. For example, antimicrobials may include, without being limited to, magnesium oxide, zinc oxide, calcium oxide, baking soda, hexamidine, magnesium carbonate, zinc carbonate, thymol, magnesium hydroxide, magnesium hydroxide and magnesium carbonate hydroxide (dead sea salt), partially carbonated magnesium hydroxide, sodium carbonate, calcium carbonate, magnesium carbonate hydroxide, cinnamon essential oil, cinnamon bark essential oil, cinnamic aldehyde, polyvinyl formate, salycilic acid, niacinamide, phenoxyethanol, eugenol, linolenic acid, dimethyl succinate, citral, triethyl citrate, sepiwhite, an substituted or unsubstituted 2-pyridinol-N-oxide material (piroctone olamine), and combinations thereof. The deodorant stick may be free of or substantially free of a substituted or unsubstituted 2-pyridinol-N-oxide material.

In general, the total amount of antimicrobial used in the present invention may be from about 0.1% to about 30%, by weight, of the deodorant. Some antimicrobials may be used in amounts as low as about 0.1%, by weight of the deodorant stick, such as if using piroctone olamine or hexamidine as the primary antimicrobial, while others could be as high as about 25% if using magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Any of the antimicrobials of the present invention may be used as powders. It is believed that antimicrobial powders may provide a better deposition and have more longevity on the skin than antimicrobials delivered in a different form. In addition, it is believed that antimicrobial powders of a certain average particle size, typically from about 1 micron to about 5 microns, may provide a significant increase in antimicrobial efficacy.

Many antimicrobials can be effective at minimizing the skin surface bacteria. However, as a leave-on product where odor may not occur until later, even hours after application, deodorant antimicrobials are needed that will be effective for long periods of time. So while deodorant antimicrobials may be effective immediately upon application on the skin, it is believed that odor comes back quickly because the bacteria living around the hair follicle can quickly repopulate the skin surface bacteria. Historical approaches using high skin penetrating liquid antimicrobials to affect this region (for example, hexanediol) can cause irritation. Therefore, the present invention may target methods and mechanisms that can more effectively deliver antimicrobials not only to the skin surface, but to the bacteria in and around the hair follicle. While not wanting to be bound to the theory, the inventors of the present inventor believe that powders, specifically powders with an average particle size of less than about 10 microns, in some cases from about 1 micron to about 5 microns, are more efficient at getting into the hair follicle where the bacteria live and repopulate the skin surface. In some embodiments, the antimicrobials may be a combination of larger sized particles and smaller particles that are from 1 to 10 microns. As noted above, solids such as powders can impact the overall hardness of the deodorant stick. In general, greater amounts of powders and structurants increase the deodorant stick's hardness.

The present inventors have discovered that the water solubilities of certain components in the solid stick deodorant have great importance. Some deodorant ingredients will bring in moisture to the batch, which can solvate these components to different extents when the water evaporates and subsequently recondenses as free water in the batch. Certain batch processing conditions (such as a closed top on the tank) could more effectively trap this water in the tank, where it is then free to interact with components of the batch. For example, highly water-soluble alkaline powders can contribute negatively towards natural and essential oil stability when dissolved. This is because many natural and essential oils contain a broad range of perfume chemicals, many of which can undergo degradation reactions when exposed to extreme pH or heat. This is why many natural and essential oils have shorter shelf lives than many commercial synthetic chemicals or perfumes. And certain antimicrobials may cause irritation due to high water solubility. Further, high water solubility can lead to grittier products as the more water-soluble powders can agglomerate when exposed to moisture released from powders during the heat of manufacture.

Thus, embodiments of the present invention may include an antimicrobial with a low water solubility. An antimicrobial with a low water solubility may be, in some embodiments, an antimicrobial with a water solubility of at most 90 g/L at 25° C., in other embodiments at most 75 g/L at 25° C., or in still other embodiments at most 50 g/L at 25° C.

Materials with a water solubility above 90 g/L @25° C. include but are not limited to: potassium carbonate, potassium bicarbonate, sodium carbonate, sodium sesquicarbonate, triethyl citrate, and baking soda. Materials with a water solubility below 90 g/L @25° C. include but are not limited to: beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, citral, and triethyl citrate. Each of beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, and citral have a water solubility below 75 g/L @25° C., below 50 g/L @25° C., below 1 g/L @25° C., and below 0.2 g/L @25° C.

D. Antimicrobial Activity

Table 2 below shows the raw material microbial inhibition concentration data tested against two key underarm bacteria strains. As can be seen, the first three listed antimicrobials, lupamin, hexamidine, and piroctone olamine, perform particularly well against the bacteria as raw materials. Also performing well as raw materials are phenoxyethanol, eugenol, linolenic acid, dimethyl succinate, citral, triethyl citrate, and sepiwhite. Also performing moderately well against the bacteria as raw materials were magnesium carbonate/magnesium hydroxide and calcium carbonate. The Tier 1 Anaerobic MIC Assay test method to generate the data of Table 2 is described below.

TABLE 2

| Antimicrobial | C. mucofaciens | S. epidermidis |
| --- | --- | --- |
| Lupamin | <2 ppm | 4 ppm |
| Hexamidine 36 mg/ml H2O | <2 ppm | 7 ppm |
| 100 mg/ml piroctone olamine in H2O | < 5 ppm | 10 ppm |
| 100% Phenoxyethanol | 400 ppm | 800 ppm % |
| Eugenol 99% ETOH | 773 ppm | 773 ppm |
| Linolenic Acid 70% ETOH | 1093 ppm | 1093 ppm |
| Dimethyl Succinate 98% ETOH | 1531 ppm | 3062 ppm |
| Citral 96% ETOH | 1500 ppm | 1500 ppm |
| 100% Triethyl citrate | 1600 ppm | 1600 ppm |
| Sepiwhite 40 mg/ml H2O ins | 2000 ppm | 1000 ppm |

TABLE 2-continued

| Antimicrobial | C. mucofaciens | S. epidermidis |
|---|---|---|
| Magnesium Carbonate & Magnesium Hydroxide 50 mg/ml H2O ins | >2500 ppm | >2500 ppm |
| Ca Carbonate 50 mg/ml H2O ins | >2500 ppm | >2500 ppm |
| Linoleic acid 100% ETOH | 3125 ppm | 3125 ppm |
| Conarom B (beta Bio) 100% ETOH | 3125 ppm | 3125 ppm |
| Hexyl Decanol 97% ETOH | 6062 ppm | 3031 ppm |
| Ajowan oil 50% ETOH | 12500 ppm | 6300 ppm |
| Oregano oil 50% ETOH | 12500 ppm | 6300 ppm |
| 100% Ethylhexyl glycerin | 12500 ppm | 12500 ppm |
| Mineral oil 50% in ETOH | 12500 ppm | >50000 ppm |
| ACH 50% in H2O | 25000 ppm | 25000 ppm |
| NaCl 250 mg/ml H2O | >25000 ppm | >25000 ppm |
| Farnesol 95% ETOH | 47500 ppm | 5937 ppm |
| Phytol 97% ETOH | >49000 ppm | >49000 ppm |
| Nerolidol 98% ETOH | >49000 ppm | >49000 ppm |
| CaCl 500 mg/ml H2O | >50000 ppm | >50000 ppm |
| Isopropyl Myristate 98% ETOH | >59000 ppm | >59000 ppm |

E. Additional Antimicrobials

The present invention may include one or more antimicrobial compositions. For example, antimicrobials may include, without being limited to, baking soda, hexamidine, magnesium carbonate, zinc carbonate, thymol, magnesium hydroxide, magnesium hydroxide and magnesium carbonate hydroxide (dead sea salt), partially carbonated magnesium hydroxide, sodium carbonate, calcium carbonate, magnesium carbonate hydroxide, cinnamon essential oil, cinnamon bark essential oil, cinnamic aldehyde, polyvinyl formate, salycilic acid, niacinamide, phenoxyethanol, eugenol, linolenic acid, dimethyl succinate, citral, triethyl citrate, sepiwhite, magnesium oxide, zinc oxide, calcium oxide, an substituted or unsubstituted 2-pyridinol-N-oxide material (piroctone olamine), and combinations thereof. The deodorant stick may be free of or substantially free of a substituted or unsubstituted 2-pyridinol-N-oxide material.

In general, the total amount of antimicrobial used in the present invention may be from about 0.1% to about 30%, by weight, of the deodorant. Some antimicrobials may be used in amounts as low as about 0.1%, by weight of the deodorant stick, such as if using piroctone olamine or hexamidine as the primary antimicrobial, while others could be as high as about 25% if using magnesium oxide, magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Perfume

Perfumes are often a combination of many raw materials, known as perfume raw materials. Any perfume suitable for use in a deodorant composition may be used herein. In some embodiments, the deodorant composition may be free of, or substantially free of a synthetic fragrance. A synthetic fragrance is one mostly derived through chemical synthesis where the starting material is no longer intact, but is converted to the new fragrance chemical.

A natural or essential oil fragrance is a result of natural sources wherein the fragrance material is not altered (chemically modified) but extracted from its natural source. These sources can include, but are not limited to, bark, flowers, blossoms, fruits, leaves, resins, roots, bulbs, and seeds. Natural or essential oils go through an extraction process instead of chemical synthesis. Extraction processes include, but are not limited to, maceration, solvent extraction, distillation, expression of a fruit peel, or effleurage.

Additional Chassis Ingredients

Starch

The deodorant composition may comprise a starch powder for dry feel or wetness absorption. Examples include but are not limited to arrowroot powder, tapioca starch, barley starch, tapioca bath starch and corn starch.

Solvent

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous deodorant compositions of the present invention may further comprise any optional material that is known for use in antiperspirant and deodorant compositions or other personal care products, or which is otherwise suitable for topical application to human skin.

One example of an optional ingredient is a scent expression material. Scent expression or release technology may be employed with some or all of the fragrance materials to define a desired scent expression prior to use and during use of the deodorant products. Such scent expression or release technology can include cyclodextrin complexing material, like beta cyclodextrin. Other materials, such as, for example, starch-based matrices or microcapsules may be employed to "hold" fragrance materials prior to exposure to bodily-secretions (e.g., perspiration). The encapsulating material may have release mechanisms other than via a solvent; for example, the encapsulating material may be frangible, and as such, rupture or fracture with applied shear and/or normal forces encountered during application and while wearing. A microcapsule may be made from many materials, one example is polyacrylates.

Another example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, chelants, and so forth. Examples of such optional materials are described in U.S. Pat. No. 4,049,792 (Elsnau); U.S. Pat. No.

5,019,375 (Tanner et al.); and U.S. Pat. No. 5,429,816 (Hofrichter et al.); which descriptions are incorporated herein by reference.

Method of Making

The deodorant stick products of the present invention may be made by mixing all the components of the products in an open-top or vented tank. Many powders come with bound moisture, especially naturally high moisture powders like starches. In a mostly anhydrous process with waxes, melting the waxes above their melt point can release this bound water as the batch temperature increases. In a closed tank process this water vapor will condense in the tank and drip back into the batch as water. This water can interact with the most water soluble ingredients in the batch to have negative effects on the product, including releasing the pH of any antimicrobial ingredient, which can then degrade any perfume ingredients in the batch. Additionally, the condensed water can interfere with the wax and produce a stick softer than intended.

The present invention reduces the risk of these negative consequences. The ideal process remedy for this behavior is to produce the batches in one of four ways:

1. An open tank system where the water vapor can leave the batch tank to reduce or eliminate condensation.
2. A vented closed tank to also remove water vapor during the batch process.
3. A dual phase process where the moisture containing powders can be put into the cold phase separate from the wax phase which is heated. These two phases are then mixed before filling.
4. A low residence time batch process for a closed system, where the product has less than 3 hours residence time above 50° C. to reduce the rate of reaction from the moisture.

A method of making a deodorant composition or stick may comprise the steps of combining any of the herein described deodorant composition components in an open tank system or a vented closed tank. The components may be mixed, heated, and then cooled into a stick product. In some embodiments, the deodorant components may comprise at least about 40% of a liquid triglyceride, by weight of the composition, and an antimicrobial in an open tank system, heating the components, mixing the components, and cooling the components.

Test Methods

Hardness Test Method—Penetration Measurement for Deodorant Finished Products

The penetration test is a physical test method that provides a measure of the firmness of waxy solids and extremely thick creams and pastes with penetration values not greater than 250 when using a needle for D1321. The method is based on the American Society for Testing and Materials Methods D-5, D1321 and D217 and DIN 51 579 and is suitable for all solid antiperspirant and deodorant products.

A needle or polished cone of precisely specified dimensions and weight is mounted on the bottom of a vertical rod in the test apparatus. The sample is prepared as specified in the method and positioned under the rod. The apparatus is adjusted so that the point of the needle or cone is just touching the top surface of the sample. Consistent positioning of the rod is critical to the measured penetration value. The rod is then released and allowed to travel downward, driven only by the weight of the needle (or cone) and the rod. Penetration is the tenths of a millimeter travelled following release.

| APPARATUS | SUGGESTED TYPE (OR EQUIVALENT) |
| --- | --- |
| Penetrometer with Timer | Penetrometer Suitable For ASTM D-5 and D-1321 methods; Examples: Precision or Humboldt Universal Penetrometer (Humboldt Manufacturing, Schiller Park, IL USA) or Penetrometer Model PNR10 or PNR12 (Petrolab USA or PetroTest GmbH). |
| Penetration Needles | Antiperspirant or deodorant solids can use: Needles as specified for ASTM Method D-5, NIST Certified, Fisher Scientific #01-512. Needles as specified for ASTM Method D 1321/DIN 51 579, Officially certified, Taper-Tipped needle, No. H-1310, Humboldt Mfg. |

General Instructions—All Penetrometers—Keep the instrument and needles/probes clean at all times, free from dust and grime. When not in use, store needles in a suitable container to avoid damage. Periodic calibration should confirm:

Electronic Timer is correctly set. Verify against an independent stopwatch if unsure.

Shaft falls without visible signs of frictional resistance.

Ensure the total weight of the shaft and needle is 50±0.2 grams when the shaft is in free fall. Note: for modern, automated or digital systems this may be performed automatically and confirmed through annual calibration.

At time of use confirm:

Electronic Timer is correctly set to 5.0 seconds.

The appropriate needle is installed and is clean, straight and without obvious defects (visual inspection)

The penetrometer is level and the shaft is clean, straight and falls freely (visual inspection)

Once level, avoid shifting the position of the unit to maintain level.

Sample Preparation and Measurement

1. On a deodorant stick that has cooled ambiently to a temperature between 22° C. and 26° C. for at least 24 hours, slice off top ½ inch of product to achieve a flat surface with a wire cutter drawn across the upper lip of the canister. This will be the reading for the Top of the stick.
2. For the first sample to be tested, lubricate the ASTM D-5 needle by gently wiping with a lint-free tissue coated with a small amount of the product to be tested. This small amount is typically taken from the shaved top.
3. Place the canister in the appropriate location for the measurement. Locate the sample so the needle will penetrate the product 9-11 mm from the inside of the canister wall on the long axis.
4. Using the coarse and fine adjustments, align the height of the penetrometer mechanism head so that the point of the penetrating needle is just touching the surface of the sample.

A weak light at the side of the penetrometer which casts a shadow of the needle on the surface of the sample may be helpful in determining this contact. When a light area on the sample cannot be seen at the end of the tip of the needle's shadow, the needle height over the sample is correctly adjusted. The light should not be strong enough to heat or melt the sample surface. The needle should be just close enough to scratch the sample surface.

5. Perform the penetration measurement at this location by releasing the needle. Record the result.

6. Repeat Steps 2 through 4 at the other test point, i.e., at the other point 9-11 mm inside of the canister wall on the long axis.

To report results, units for penetration are tenths of a millimeter (1/10 mm=100 microns). For example, a result of 80 units is 80 mm*10 or 8 mm. Report the average results of at least 4 total measurements from 2 different sticks, report to the nearest tenth of a millimeter.

7. For the Bottom of the stick measurements, turn the canister up until only 1-2" of product is left on the elevator. slice the product to achieve a flat surface with a wire cutter drawn across the upper lip of the canister. Then repeat Steps 2-6 to measure and record the Bottom of the stick harness. The average of the Top and Bottom reading is the hardness of the stick.

Oil Binding Capacity Test Method

The Oil Binding Capacity Test Method is used to measure the fraction of the composition of a stick retained under conditions of centrifugation. Preweighed specimens of sample composition are each placed in a centrifuge equipped with a filter is subjected to 800 G of centrifugal force for 20 minutes, and the mass of each specimen passing through the filter and collected in the tube is then measured, from which each retained specimen fraction is calculated. This method is carried out in an environment 23±2° C. and 50±5% relative humidity environment unless otherwise specified, and all materials and apparatus used are allowed to equilibrate to lab conditions for at least two hours prior to use.

At least three specimens of composition are collected and individually analyzed from each of the top 0.8-cm layer, the middle 0.8-cm layer, and the bottom 0.8-cm layer of a freshly opened product stick. A transfer tube (such as part number 190195P, Repligen Corporation, Boston, Mass., USA, or equivalent) is used to harvest each specimen, 0.75±0.25 g in mass. Each specimen plug of sample composition in the transfer tube is pushed into a preweighed filter unit of a filter centrifuge tube (Spin-X-Mfr #8169 Costar, Inc., Corning, N.Y., USA or equivalent) and the mass of the specimen is determined by difference and recorded to the nearest 0.0001 g. Each centrifuge tube is separately preweighed from the loaded filter unit, and its mass is recorded to the nearest 0.0001 g. Each loaded filter unit and centrifuge tube assembly containing a specimen is subjected to centrifugation at 800 G for 20.0 minutes. (One example of suitable centrifuge apparatus and RPM setting to achieve this is the Sorvall Legend Micro 21, Thermo Fisher Scientific, USA, operated at 3000 RPM). Immediately after centrifugation, the filter unit is removed from each filter-unit-and-centrifuge-tube assembly, and the mass of the centrifuge tube and containing expressed product composition is recorded to the nearest 0.0001 g, from which the mass of product expressed from each specimen is calculated by difference to the nearest 0.0001 g. The mass of specimen retained in the filter is defined as the oil binding capacity and defined for each specimen as:

$$\text{specimen oil binding capacity}[\%] = 100\% \times \left(1 - \frac{\text{mass of expressed product composition [g]}}{\text{mass of specimen [g]}}\right).$$

The arithmetic mean of all specimens taken from the top layer of the product stick is calculated and recorded to the nearest 0.1% as the top layer oil binding capacity. The arithmetic mean of all specimens taken from the middle layer of the product stick is calculated and recorded to the nearest 0.1% as the middle layer oil binding capacity. The arithmetic mean of all specimens taken from the bottom layer of the product stick is calculated and recorded to the nearest 0.1% as the bottom layer oil binding capacity. The arithmetic mean of the top layer oil binding capacity, the middle layer oil binding capacity, and the bottom layer oil binding capacity is calculated to the nearest 0.1% and reported as the Oil Binding Capacity of the stick.

Tier 1 Anaerobic MIC Assay

The data in Table 2 above was generated with the following test method. The purpose of this assay is to determine if a compound or formulation has an antimicrobial effect in vitro.

It is understood that when not specifically noted in this procedure:

a) All materials, reagents and equipment required for this procedure are of appropriate design and condition of cleanliness and/or sterility as determined by their intended use.

b) The operator has been trained in aseptic technique and has been qualified to perform the procedure and accurately interpret the results.

c) All media required for this procedure was manufactured by a reputable commercial source egg. Difco, Merck etc. and has been stored and prepared as per manufacturer's instructions.

d) All routine laboratory controls, including but not limited to, media function and growth promotion tests, verification of sterility and use of positive and negative controls are being conducted.

Procedure: (All procedures performed in anaerobic chamber except where noted)

1. Apparatus

Incubator at 37° C.; 20-200 ul 12 channel pipette; 5-50 ul 12 channel pipette; 1250 ul 8 channel Thermo Scientific Matrix pipette; 96 well plate shaker (located in incubator); Beckman Coulter deep well cap mat #267005; Beckman Coulter deep 96 well plates #267007; Falcon 96 well tissue culture plates #353072; Vortexer; Culture tubes/caps Disposable sterile gloves; Sterile petri dishes; Standard microbiological lab equipment (sterile pipettes, syringes, tips, loops, etc.); Glass bottles/flasks for media; Autoclave; Parafilm; Spectrophotometer.

2. Media 0.9% or 0.85% saline solution

BHI agar supplemented with 1% Tween 80

BHI media supplemented with 1% Tween 80

3. Microbial Strains

*Staphylococcus epidermidis* (clinical isolate)

*Corynebacterium mucofaciens* (clinical isolate)

4. Test Procedure

Inoculum Preparation

Prior to testing streak organisms for isolation on BHI with 1% Tween 80 plates, wrap with parafilm and place in 37° C. incubator. When isolated colonies appear remove one representative colony from each plate and place each in 5 ml of BHI with 1% Tween 80 media. Incubate at 37° C. with shaking overnight. Inoculate 20 ml BHI with 1% Tween 80 (per 96 deep well plate to be tested) with 20 ul of the overnight culture (1-1000 dilution).

Master Plate Preparation

Compounds/formulations to be tested are diluted across a 96 deep well plate as shown below in Table 3 (for a 1% stock solution). 800 ul of 0.85% saline is added to wells A1 and B1 (as these will be the negative and positive control respectively). 800 ul each 1% stock solution+ positive control are added to wells C1 through H1. 400 ul 0.85% saline are added to all other wells. 400 ul is then removed from #1 well added to the #2 well and mixed. This is then continued across the plate resulting in a 50% dilution between wells across the plate (this can be easily accomplished with an automatic 8 channel Matrix pipette set to withdraw, dispense and mix).

TABLE 3

| | 1 | 2 | 3 | 4 | 5 | 6 |
|---|---|---|---|---|---|---|
| A | 800 ul saline | 400 ul NaCl | 400 ul NaCl | 400 ul NaCl | 400 ul NaCl | 400 ul NaCl |
| B | 800 ul saline | 400 ul NaCl | 400 ul NaCl | 400 ul NaCl | 400 ul NaCl | 400 ul NaCl |
| C | 800 ul + control | 400 ul NaCl | 400 ul NaCl | 400 ul NaCl | 400 ul NaCl | 400 ul NaCl |
| D | 800 ul compound 1 | 400 ul NaCl | 400 ul NaCl | 400 ul NaCl | 400 ul NaCl | 400 ul NaCl |
| E | 800 ul compound 2 | 400 ul NaCl | 400 ul NaCl | 400 ul NaCl | 400 ul NaCl | 400 ul NaCl |
| F | 800 ul compound 3 | 400 ul NaCl | 400 ul NaCl | 400 ul NaCl | 400 ul NaCl | 400 ul NaCl |
| G | 800 ul compound 4 | 400 ul NaCl | 400 ul NaCl | 400 ul NaCl | 400 ul NaCl | 400 ul NaCl |
| H | 800 ul compound 5 | 400 ul NaCl | 400 ul NaCl | 400 ul NaCl | 400 ul NaCl | 400 ul NaCl |

| | 7 | 8 | 9 | 10 | 11 | 12 |
|---|---|---|---|---|---|---|
| A | 400 ul NaCl | 400 ul NaCl | 400 ul NaCl | 400 ul NaCl | 400 ul NaCl | 400 ul NaCl |
| B | 400 ul NaCl | 400 ul NaCl | 400 ul NaCl | 400 ul NaCl | 400 ul NaCl | 400 ul NaCl |
| C | 400 ul NaCl | 400 ul NaCl | 400 ul NaCl | 400 ul NaCl | 400 ul NaCl | 400 ul NaCl |
| D | 400 ul NaCl | 400 ul NaCl | 400 ul NaCl | 400 ul NaCl | 400 ul NaCl | 400 ul NaCl |
| E | 400 ul NaCl | 400 ul NaCl | 400 ul NaCl | 400 ul NaCl | 400 ul NaCl | 400 ul NaCl |
| F | 400 ul NaCl | 400 ul NaCl | 400 ul NaCl | 400 ul NaCl | 400 ul NaCl | 400 ul NaCl |
| G | 400 ul NaCl | 400 ul NaCl | 400 ul NaCl | 400 ul NaCl | 400 ul NaCl | 400 ul NaCl |
| H | 400 ul NaCl | 400 ul NaCl | 400 ul NaCl | 400 ul NaCl | 400 ul NaCl | 400 ul NaCl |

| | 1 | 2 | 3 | 4 | 5 | 6 |
|---|---|---|---|---|---|---|
| A | Media Blank | Media Blank | Media Blank | Media Blank | Media Blank | Media Blank |
| B | Pos | Pos | Pos | Pos | Pos | Pos |
| C | 0.1 | 0.05 | 0.025 | 0.0125 | 0.00625 | 0.003125 |
| D | 0.1 | 0.05 | 0.025 | 0.0125 | 0.00625 | 0.003125 |
| E | 0.1 | 0.05 | 0.025 | 0.0225 | 0.00625 | 0.003125 |
| F | 0.1 | 0.05 | 0.025 | 0.0125 | 0.00623 | 0.003125 |
| G | 0.1 | 0.05 | 0.025 | 0.0125 | 0.00625 | 0.003125 |
| H | 0.1 | 0.05 | 0.025 | 0.0225 | 0.00625 | 0.003125 |

| | 7 | 8 | 9 | 10 | 11 | 12 |
|---|---|---|---|---|---|---|
| A | Media Blank | Media Blank | Media Blank | Media Blank | Media Blank | Media Blank |
| B | Pos | Pos | Pos | Pos | Pos | Pos |
| C | 0.0015625 | 0.00073125 | 0.000390625 | 0.000195313 | 9.76563E−05 | 4.88281E−05 |
| D | 0.0015625 | 0.00078125 | 0.000390625 | 0.000135333 | 9.76563E−05 | 4.88281E−05 |
| E | 0.0015625 | 0.00078125 | 0.000390625 | 0.000195313 | 9.76563E−05 | 4.88281E−05 |
| F | 0.0015625 | 0.00078125 | 0.000390625 | 0.000195313 | 9.76563E−05 | 4.88281E−05 |
| G | 0.0015625 | 0.00078125 | 0.000350625 | 0 000195313 | 9.76563E−05 | 4.88281E−05 |
| H | 0.0015625 | 0.00078225 | 0.000390625 | 0.000195913 | 9.76563E−05 | 4.88281E−05 |

Test Plate Preparation

In row A of a 96 deep well plate pipette 180 ul of sterile BHI with 1% Tween 80 as a negative growth control. All other wells receive 180 ul of inoculum. From the master plate introduce 20 ul to the corresponding row in the test plate using an 8-channel pipette. Loaded plates are placed on a plate shaker in the 37° C. incubator and incubated overnight. The next day read the O.D. 600 on a plate reader. The MIC is the last well from the right that has no bacterial growth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All numeric values (e.g., dimensions, flow rates, pressures, concentrations, etc.) recited herein may be modified by the term "about", even if not expressly so stated with the numeric value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid deodorant stick comprising:
   a. an emollient comprising a natural or naturally-derived oil;
   b. an antimicrobial;
   c. a structurant comprising a naturally-derived wax blend and optionally one or more additional natural or naturally derived structurants; wherein the naturally-derived wax blend comprises:
  i. from about 5% to about 20% of an ester wax having a melting point of at least about 55° C., wherein the ester wax is the primary structurant;
  ii. from 0.01% to 2% of a fatty alcohol or fatty alcohol-containing wax;
  iii. optionally one or more additional naturally-derived waxes;
wherein the deodorant stick is anhydrous and substantially free of aluminum; and wherein the stick has an oil binding capacity percent of at least 80%.

2. The deodorant stick of claim 1, wherein the deodorant stick comprises a hardness at most about 140 mm*10, as measured by penetration with an ASTM D-5 needle according to the Hardness Test Method, averaging the top and bottom values of the stick.

3. The deodorant stick of claim 1, wherein the deodorant stick comprises a hardness at most about 100 mm*10, as measured by penetration with an ASTM D-5 needle according to the Hardness Test Method, averaging the top and bottom values of the stick.

4. The deodorant stick of claim 1, wherein the deodorant stick has a hardness at most about 70 mm*10, as measured by penetration with an ASTM D-5 needle according to the Hardness Test Method, averaging the top and bottom values of the stick.

5. The deodorant stick of claim 1, wherein the deodorant stick has a hardness at most about 60 mm*10, as measured by penetration with an ASTM D-5 needle according to the Hardness Test Method, averaging the top and bottom values of the stick.

6. The deodorant stick of claim 1, wherein the ester wax is chosen from behenyl behenate, stearyl stearate, stearyl palmitate, stearyl behenate, or mixtures thereof.

7. The deodorant stick of claim 1, wherein the fatty alcohol or fatty alcohol-containing wax is chosen from rice bran wax, stearyl alcohol, behenyl alcohol, cetly alcohol, oleyl alcohol, arachidyl alcohol, ceryl alcohol, or mixtures thereof.

8. The deodorant stick of claim 1, wherein the antimicrobial is chosen from beryllium carbonate, magnesium carbonate, calcium carbonate, magnesium hydroxide, magnesium hydroxide and magnesium carbonate hydroxide, partially carbonated magnesium hydroxide, piroctone olamine, potassium carbonate, potassium bicarbonate, sodium carbonate, sodium sesquicarbonate, sodium bicarbonate, hexamidine, zinc carbonate, thymol, polyvinyl formate, salycilic acid, niacinamide, magnesium carbonate hydroxide, cinnamon essential oil, cinnamon bark essential oil, cinnamic aldehyde, magnesium oxide, zinc oxide, or mixtures thereof.

9. The deodorant stick of claim 1, wherein the antimicrobial is a powder.

10. The deodorant stick of claim 1, wherein the deodorant stick further comprises a starch powder selected from the group consisting of arrowroot powder, tapioca starch, corn starch, or mixtures thereof.

11. The deodorant stick of claim 1, wherein the antimicrobial is chosen from calcium hydroxide, sodium bicarbonate, magnesium hydroxide, magnesium oxide, or mixtures thereof.

12. The deodorant stick of claim 1, wherein the natural or naturally-derived oil is a liquid triglyceride.

13. The composition of claim 12, wherein the liquid triglyceride is selected from the group consisting of caprylic/capric triglyceride, triheptanoin, and combinations thereof.

14. The deodorant stick of claim 1, wherein the natural or naturally-derived oil comprises a liquid triglyceride comprising a mixture of chain lengths from 8 to 10.

15. The deodorant stick of claim 1, wherein the antimicrobial is a powder with a water solubility of at most about 90 g/L at 25° C.

16. The deodorant stick of claim 1, wherein the hardness of the top of the deodorant stick is at most 60 mm*10, as measured by penetration with an ASTM D-5 needle according to the Hardness Test Method.

17. The deodorant stick of claim 1, wherein the hardness of the top of the deodorant stick is at most about 35 mm*10, as measured by penetration with an ASTM D-5 needle according to the Hardness Test Method.

18. The deodorant stick of claim 1, wherein the hardness of the bottom of the deodorant stick is at most about 60 mm*10, as measured by penetration with an ASTM D-5 needle according to the Hardness Test Method.

19. A solid deodorant stick comprising:
  a. a liquid triglyceride;
  b. an antimicrobial;
  c. a naturally-derived wax blend comprising:
    i. from about 7% to about 20% of behenyl behenate; and
    ii. from 0.01% to 2% of rice bran wax;
  wherein the deodorant stick is anhydrous and substantially free of aluminum;
  and wherein the stick has an oil binding capacity percent of at least 80%.

20. The deodorant stick of claim 1, wherein the emollient consists of the natural or naturally-derived oil; and wherein the structurant consists of the naturally-derived wax blend and optionally the one or more natural or naturally derived structurants.

* * * * *